United States Patent [19]
Yerman

[11] 4,233,975
[45] Nov. 18, 1980

[54] ANTI-DRUG ABUSE SINGLE-USE SYRINGE

[76] Inventor: Arthur J. Yerman, 123 William Cook Blvd., Manahawkin, N.J. 08050

[21] Appl. No.: 948,532

[22] Filed: Oct. 4, 1978

[51] Int. Cl.³ .............................................. A61M 5/00
[52] U.S. Cl. .................... 128/218 P; 128/234
[58] Field of Search ......... 128/218 P, 218 PA, 218 R, 128/218 M, 234, 215, 216, 213

[56] References Cited

U.S. PATENT DOCUMENTS

| | | | |
|---|---|---|---|
| 3,946,732 | 3/1976 | Hurscham | 128/218 M |
| 3,951,146 | 4/1976 | Arias | 128/218 P |

FOREIGN PATENT DOCUMENTS

| | | | |
|---|---|---|---|
| 110024 | 8/1968 | Denmark | 128/218 P |
| 112893 | 1/1969 | Denmark | 128/218 P |
| 2298340 | 8/1976 | France | 128/218 P |

Primary Examiner—John D. Yasko

[57] ABSTRACT

In a preferred embodiment, a tubular syringe had a separate terminal plunger portion positioned to be pushed into a position of blocking flow to and from the needle passage as the plunger proximal portion is moved inwardly to expel syringe contents, and at the blocking position a male member being locked into a female member positioned to permit movement to the blocking position but preventing withdrawal of the terminal portion from the blocking position, preventing subsequent intake or outflow through the syringe needle passage.

3 Claims, 13 Drawing Figures

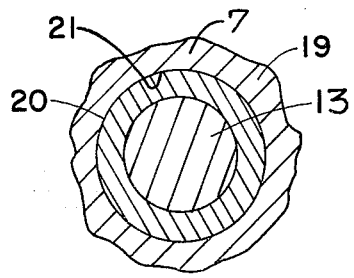
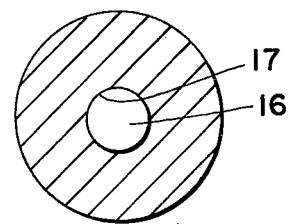
FIG. 4    FIG. 5
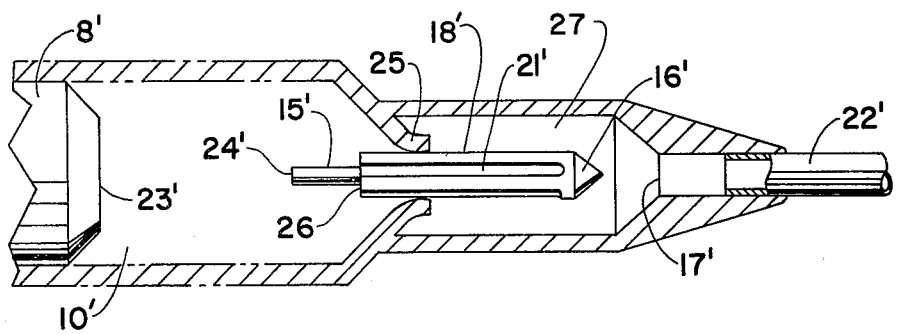
FIG. 6A
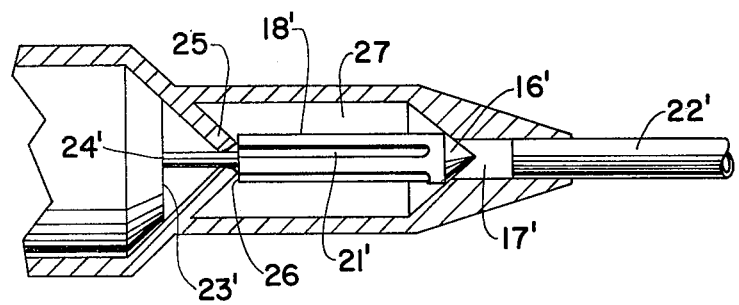
FIG. 6B

ANTI-DRUG ABUSE SINGLE-USE SYRINGE

This invention is directed to a novel syringe.

BACKGROUND TO THE INVENTION

Prior to the present invention, there has been a major problem throughout the industrial world, characterized by the United States where improper use of syringes is an integral part of the injectable drug-addiction together with other medical and criminal problems associated therewith. In particular, as of the New York Daily News article of Jan. 24, 1978 by I. D. Robbins, the narcotic users range between 500,000 and 800,000 persons, probably the latter since as long ago as 1973 the Department of Health, Education, and Welfare estimated at that time the nation's addict population to be 600,000. Whatever the number, it is of shocking and disastrous proportions, a recent Penthous magazine article stating that today 800,00 young Americans are heroin addicts, this figure believed to be conservative by Select Narcotic Committe Chairman Lester Wolff (Dem., N.Y.) and others. Moreover, hepatitis is widespread among the addict population whose dirty needles spread the disease from one addict to another; and while such disease has heretofore not been considered to be a suburban problem, such has proven otherwise as early as 1974 when New Jersey rural areas began having large numbers of cases of hepititis found thereupon to be carried by misquitoes from the cities to the suburban and rural areas. The Penthouse article cited retiring Essex County Assignment Judge Joseph B. Sugure as stating that recently 50% of all cases in his court were drug related. The same article stated that of every 125 crimes committed by a drug addict, the addict is caught only once, and that between eight and ten tons of illegal heroin are smuggled into the country each year. An addict must spend typically $50 per day to support a drug-habit on heroin, totalling $18,200 per day—such addict normally being a person without any such funds available thereby requiring the addict to turn to daily crime to support the habit, including muggings, robberies, prostitution, and the like.

It is well-known that legitimate syringes rapidly find their way into the drug market—often from the trash cans of the doctors' offices, and of clinics and hospitals; such scavanged syringes bring a high price in the drug market because of the shortage thereof and the great need therefor by the numerous addicts. Thus, a major bottle-neck for the perpetuation of the heroin-related drug-addiction, is the reusable syringe, and accordingly this is a key focal point of the present invention.

Heretofore the problem of need for an incapacitated syringe has been recognized at least once, in the U.S. Pat. No. 3,951,146 to Chiquiar-Arias on Apr. 20, 1976 directed to a blade-containing syringe which self-destructs upon a pressing of the plunger thereof during the expelling of the syringe contents in use thereof. There are other patents which have not been directed to such problem nor purpose, but which have contained unidirectional flow valves for multi-use syringes; typical in U.S. Pat. No. 3,663,752 which discloses an accessory inlet check valve that permits the accessory passage of liquid medicine only in the direction into the main path of injection, in order that the accessory injection may optionally be used with the multiple injection syringe and needle thereof. Likewise, the U.S. Pat. No. 3,727,614 discloses an accessory attachment inlet of a multiple dosage innoculator, having a check valve and also having a further cooperating coordinated check valve adjacent the needle, not preventing further use of the multiple-use syringe and needle thereof. U.S. Pat. No. 3,827,601 discloses a hand powered liquid syringe metering dispenser particularly for use in the veterinery field, with a plunger check-valve preventing reverse-flow between multiple uses thereof. Likewise, U.S. Pat. No. 4,007,739 discloses a unidirectional-flow fluid-operated hypodermic syringe for multiple-use injection of medicinal fluids into livestock. None of these unidirectional devices are directed toward nor will function as a mechanism to prevent reuse of the injection mechanism or to prevent refilling and reuse by the drug traffic.

SUMMARY OF THE INVENTION

Accordingly, objects of the present invention include the overcoming and/or avoiding of problems and difficulties of the types discussed-above, together with the obtaining of novel advantages not heretofore available.

Another object is to obtain a hypodermic syringe of inexpensive and practical construction making the same feasible for production on a commercial scal that could be contemplated for a typical syringe-producing company.

Another object is to achieve a simple and foolproof mechanism for incapacitating a hypodermic syringe, together with the forgoing objects preferably.

Another object is to obtain a syringe which effectively blocks future passage of injectables subsequent to an initial pressing of the plunger thereof to expel the syringe contents thereof.

Another object is to obtain a syringe adapted to be self-incapacitating during initial use thereof, while concurrently providing for on-site filling of the syringe by the nurse or doctor.

Another object is to provide a syringe for normal medical intravenous or sub-cutaneous use or intramuscular use, as the case may be, but particularly of the type that an allergist and other such large physician-users would find acceptable and medically sound and steril to their satisfaction.

Other objects become apparent from the preceding and following disclosure.

One or more objects of the invention are obtained by the embodiments typically illustrated in the following Figures for the primary purpose of improving understanding of the invention and typical variations thereon, such embodiments being not intended to unduly limit the scope of the invention which includes obvious equivalents and modifications and variations within ordinary skill of the ordinary artisan in this particular field.

Broadly the invention may be described as a single-use syringe typically including a tubular element and a plunger reciprocatably mounted therein inserted into the enlarged plunger-receiving opening thereof, and having a needle or needle-mounting opposite end, preferably having the needle an integral part thereof; the inventive improvement broadly is a mechanism involving a one-way movement of the plunger when the plunger is insertably moved beyond a predetermined point of substantially complete insertion at which time and point the plunger terminal end cannot be withdrawn because of it becoming locked to thereby concurrently block future flow of liquid or other fluid to or fro through the syringe outlet and needle thereof; the term "plunger" as used herein includes the entire plunging structure(s) axially aligned to expel the syringe contents. For example, the one embodiment, what is herein referred to as the terminal end portion, is a separate plug which becomes pushed by a proximal separate portion to thereby push a male member past a flexible female member's wall which flips-back to thereby lock the male member against reverse directional movement thereof whereby the pointed end of the termiend portion effectively is held within the syringe outlet in a flow-blocking state thereof. In another embodiment, the fluid-impelling plunger portion constitutes the terminal end mounted on a wedge-fitted elongated narrow shaft which becomes pulled-out of the wedged state and position when an attempt is made to withdraw the terminal end portion after the terminal end portion has been pushed sufficiently far that a male member becomes locked behind an initially depressable female flange to the flow-blocking position and state. In another embodiment, a spring-biased key is the male member and becomes spring-biased into a female space of the other one of the plunger or tube-wall, as the case may be. In embodiments in which the fluid is expelled by the proximal portion, flow-grooves or channels are located in the terminal-end portion, but which grooves or channels become blocked against further flow when the terminal-end portion becomes locked in the flow-blocking position and state.

The invention may be better understood by making reference to the following Figures.

THE FIGURES

FIGS. 6A and 6B show in-part view in side cross-section diagrammatically of an alternate embodiment also in different positions, diagrammatically representing the preinjection and the locked-position states.

Figure 9:
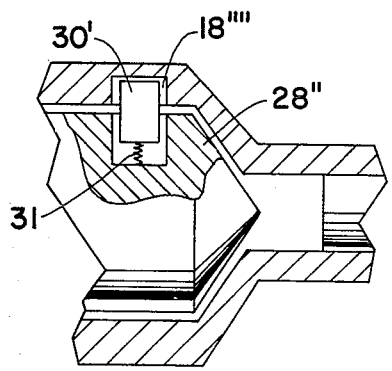

FIG. 9 gives an in-part view in side cross-section of a spring-biased key embodiment, diagrammatically.

DETAILED DESCRIPTION

Figure 1:
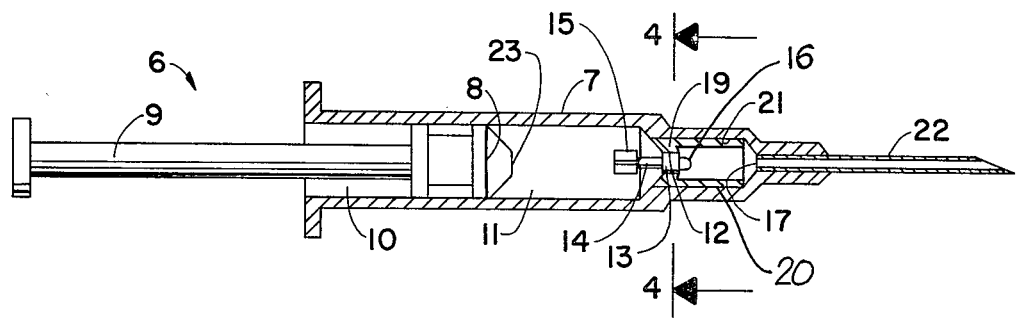
FIG. 1 illustrates a preferred embodiment diagrammatically in side cross-sectional view. Likewise.
Figure 2:
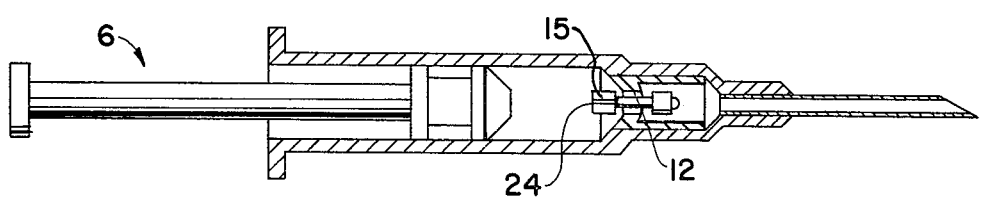
FIGS. 2 and 3 show side cross-sectional view of the same embodiment at progressively different states and stages moving to the final locked and flow-blocking position and state of FIG. 3, and the FIGS. 4 and 5 show various transverse cross-sectional views diagrammatically.
Figure 3:
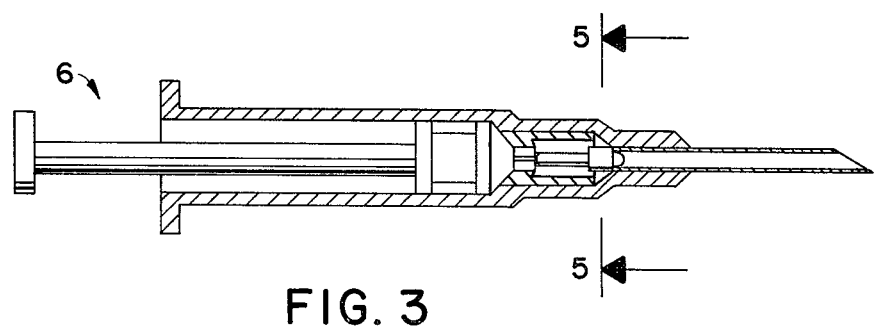

FIGS. 1 through 5 disclose a common embodiment and different phases of use thereof in FIGS. 1 through 3, for the syringe 6 having plunger proximal portion made up of shaft 9 and piston 8 and having plunger terminal-end portion made up of an intermediat narrow part 14, plug-end pointed end 13, and pressure-receiving and plug-end 15 which becomes pressed by the piston 8 as the piston 8 approaches the end of its travel stroke in the ejecting of the liquid 11 from the tubular space 10. This embodiment represents a typical prefilled syringe, preplugged by the flow plug-end 13 and eventually that pointed end serving to block flow through the outlet 17 from the intermediate compartment space 18 into which space the flexible female flanges may be slightly stretched as the plug-end 15 becomes plugged as shown in FIG. 3. The preferably blunted end 23 of the piston 8 presses against the pressure-receiving plug-end 15 to move the same axially along the tubular space 10 to the plugging position in the through-aperture 12. Entire block assembly 20 is fused against wall 21.

FIG. 4 shows a cross-sectional view as taken along line 4—4 of FIG. 1, and FIG. 5 shows a cross-sectional view as taken along lines 5—5 of FIG. 3.

FIGS. 6A and 6B illustrates a plunger proximal portion separate from the plunger terminal portion, the plunger terminal-end portion including the pressure-receiving end 15 having flattened face 24' to be pressed by flattened pusher surface 23' of the plunger proximal portion 8'. The plunger terminal-end portion further includes the main body 18' having by-pass flow grooves or channels 21' and plugging pointed end 16' which as shown in the FIG. 6B blocks flow to the outlet 17' while the female members 25 have snapped closed behind the male member face 26. In the FIG. 6A position, flow from space 10' to space 27 through the grooves or channels 21'.

Figure 7C:
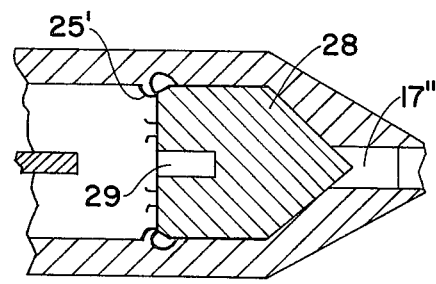
FIGS. 7A and 7C show diagrammatically another embodiment in side cross-sectional in-part views, and FIG. 7B gives a typical cross-section transversely.
Figure 7A:
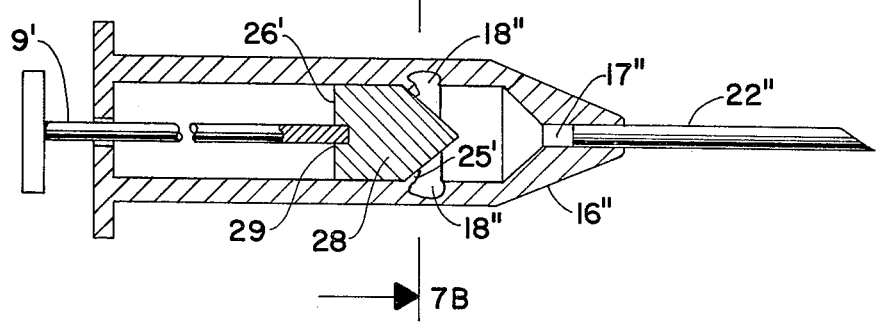
Figure 7B:
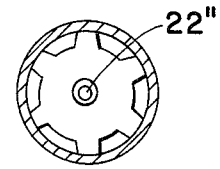

In the FIGS. 7A, 7B, and 7C embodiment, the plunger shaft 9' is the proximal end portion wedge-fitted into the aperture 29 of the terminal-end portion 28. The terminal end portion's pointed end 16'' effectively blocks flow through outlet 17 when the female members 25 flexibly and resiliently snap-back into locking positions and states after being depressed into spaces 18'', blocking flow into or from needle 22''.

Figure 8B:
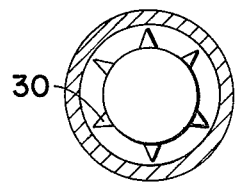
FIG. 8A illustrates diagrammatically in side cross-sectional in-part view a still other embodiment of the invention, and the FIG. 8B shows a typical cross-sectional view.
Figure 8A:
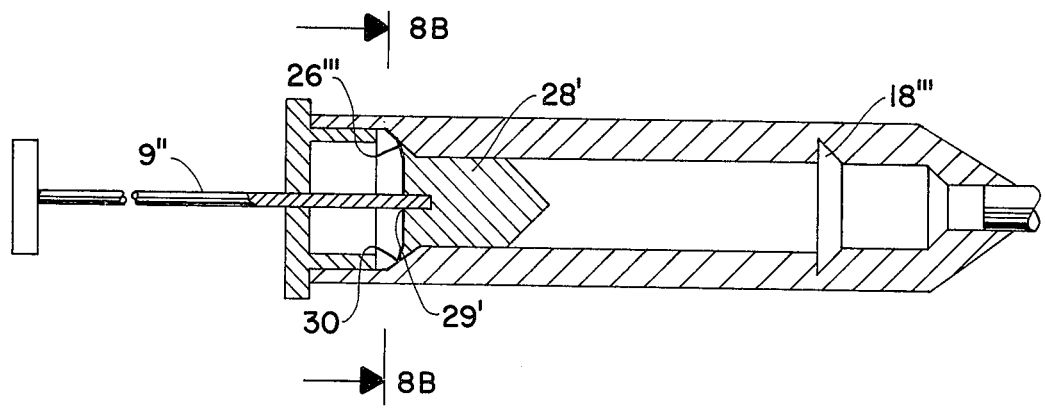

In the FIG. 8A embodiment, the flexible flange 30 is a part of the male member 26''', locking into the female space 18''', the flanges-male members also being viewable in FIG. 8B, of the terminal-end portion 28'; as in the FIG. 7A embodiment, the proximal portion 9'' (plunger shaft) is wedge-fitted and pulls-out of the wedg-aperture 29' when an effeort is made to withdraw the terminal-end portion 28' from its locked state and position.

FIG. 9 in an in-part view illustrates another embodiment, in which the female space receives male key member 30' spring-biased by biasing spring 31 typically as a plastic coil spring or a resilient rubber or plastic or the like, which male key member snaps into the locked position whenever the terminal-end portion 28'' is pushed-in toward the blocking portion far enough to align the male structure with the female structure. Otherwise, the embodiment of FIG. 9 is of a structure of FIG. 8A, for example, although any of the other embodiments' structures might also be followed otherwise.

Accordingly, for any of the foregoing embodiments, once the plunger is pressed to a fully-expelling position, the flow path to the needle becomes forever-blocked, and cannot be reopened except by tearing-apart the structure of the syringe, and in so-tearing, the utility of the syringe would be destroyed, preventing its reuse by drug addicts.

As to the FIGS. 1 through 5 embodiment, this embodiment is optimally adapted to be a prefilled syringe, ready for use as purchased, and some of the benefits of such an arrangement are as follows:

1. The fluid contents does not come in contact with the needle's interior prior to injection, which can be a cause of needle corrosion and contamination in situations where there is such contact.

2. Present pre-filled syringes (prior to the present inventive embodiments) plugged the cannula at its tips, thereby "dulling" the point with rubber shield.

3. The present double "belleville" washer design permits low pressure shifting of the spool as well as rigid section to prevent back-shifting of the spool.

4. The pre-filled present inventive embodiment design eliminates possible septum "coring" as is disadvantageously characteric a drawback (the presence of coring) in syringes such as shown in U.S. Pat. No. 3,375,825 (Keller), or when filing a syringe from a vial (vial septum).

It should be further noted, that it is within the scope of the invention to add a barb or the like to a side of a forward end of elements such as 27 (FIG. 6A) and/or 13 (FIG. 1) which when mounting will be pressed into space the lock space such as 18' thereby preventing removal (as with tweezers) of the plug member once inserted into its operational position such as shown (operational position) in FIGS. 6A and 1, for example.

I claim:

1. A single-use syringe comprising in combination: a tubular element having a plunger reciprocatably mounted in a first open end to tubular space of the tubular element and having an injection needle operably mounted on a remaining opposite end of the tubular element, a hollow portion of needle-through-space being in flow communication with tubular space of the tubular element, the improvement being at least one of (a) an interior wall of the tubular element and (b) a circumscribing lengthwise-wall of the plunger, including a male member and the other thereof including a female member preventing retraction of a terminal end-portion of the plunger when the plunger is inserted within the tubular space sufficiently for the male member to become aligned with the female member, at least one of the male member and the female member being movable such that the male member is lockable into the female member, whereby a non-reusable syringe results preventing refilling or reinjection in use thereof, said plunger including a terminal end that blocks further outflow of syringe contents when said male member is mated with said female member, and said plunger including a separable proximal end jointly movably axially to and fro prior to and until said male member is mated with said female member, said proximal end being detachable from said terminal end when withdrawal pressure is applied to said proximal end after the male member is mated with the female member whereby the terminal end continues to block outflow of syringe contents when an effort is made to withdraw the plunger.

2. A single-use syringe comprising in combination: a tubular element having a plunger recirocatably mounted in a first open end to tubular space of the tubular element and having an injection needle operably mounted on a remaining opposite end of the tubular element, a hollow portion of needle-through-space being in flow communication with tubular space of the tubular element, the improvement being at least one of (a) an interior wall of the tubular element and (b) a circumscribing lengthwise-wall of the plunger, including a male member and the other thereof including a female member with each of said male member and said female member being positioned such that the male member locks into the female member preventing retraction of a terminal end-portion of the plunger when the plunger is inserted within the tubular space sufficiently for the male member to become aligned with the female member, at least one of the male member and the female member being movable such that the male member is lockable into the female member, whereby a non-reusable syringe results preventing refilling or reinjection in use thereof, said plunger including a terminal end and a separate proximal end, movement of said proximate end against said terminal end sufficiently to align said male member with said female member being adapted to position said terminal end to a thereafter blocking position at which the terminal end blocks further flow of syringe contents through a needle end of the tubular element.

3. A single-use syringe of claim 2, in which said terminal end includes at-least one by-pass channel communicating with tubular space at both a needle-end and the first open end of the tubular element except when said terminal end is locked when the male member is mated with the female member.

* * * * *

Notice of Adverse Decision in Interference

In Interference No. 100,696, involving Patent No. 4,233,975, A. J. Yerman, ANTI-DRUG ABUSE SINGLE-USE SYRINGE, final judgment adverse to the patentee was rendered Sept. 7, 1982, as to claim 1.

[*Official Gazette Feb. 1, 1983.*]